US 11,680,887 B1

(12) United States Patent
Zhang et al.

(10) Patent No.: US 11,680,887 B1
(45) Date of Patent: Jun. 20, 2023

(54) DETERMINING ROCK PROPERTIES

(71) Applicant: Saudi Arabian Oil Company, Dhahran (SA)

(72) Inventors: Jilin Jay Zhang, Cypress, TX (US); Hui-Hai Liu, Katy, TX (US); Jewel Duncan, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/540,013

(22) Filed: Dec. 1, 2021

(51) Int. Cl.
*G01N 15/08* (2006.01)
*G01F 1/80* (2006.01)
*G01N 33/24* (2006.01)

(52) U.S. Cl.
CPC ......... *G01N 15/0826* (2013.01); *G01N 15/08* (2013.01); *G01N 15/082* (2013.01); *G01N 15/0806* (2013.01); *G01N 33/24* (2013.01); *G01N 2203/0019* (2013.01)

(58) Field of Classification Search
CPC ............... G01N 15/0826; G01N 15/08; G01N 15/0806; G01N 15/082; G01N 33/24; G01N 2203/0019; G01F 1/80
See application file for complete search history.

(56) References Cited

U.S. PATENT DOCUMENTS

| | | | |
|---|---|---|---|
| 2,801,698 A | 8/1957 | Bond | |
| 4,135,579 A | 1/1979 | Rowland et al. | |
| 4,193,451 A | 3/1980 | Dauphine | |
| RE30,738 E | 9/1981 | Bridges et al. | |
| 4,345,650 A | 8/1982 | Wesley | |
| 4,389,878 A | 6/1983 | Manzie, Jr. | |
| 4,444,058 A | 4/1984 | Ratigan | |
| 4,485,869 A | 12/1984 | Sresty | |
| 4,587,739 A | 5/1986 | Holcomb | |
| 4,665,982 A | 5/1987 | Brown | |
| 4,665,990 A | 5/1987 | Perlman | |

(Continued)

FOREIGN PATENT DOCUMENTS

| | | |
|---|---|---|
| CN | 1621803 | 6/2005 |
| CN | 101819111 | 9/2010 |

(Continued)

OTHER PUBLICATIONS

U.S. Appl. No. 16/998,243, filed Aug. 20, 2020, Zhang et al.

(Continued)

*Primary Examiner* — Ryan D Walsh
(74) *Attorney, Agent, or Firm* — Fish & Richardson P.C.

(57) ABSTRACT

A method for determining a rock property includes positioning a core sample in a core sample assembly that is enclosed in a pressurized container with a flow inlet, a flow outlet, and a pressurized fluid inlet fluidly coupled to a pressurized fluid reservoir that includes a pressurized fluid pump; sequentially performing at least three test operations on the core sample; at each of the at least three test operations, measuring an inlet pressure at the flow inlet, measuring an outlet pressure at the flow outlet, and measuring a confining pressure within the pressurized container; and determining a permeability of the core sample based at least in part on at least one of the measured inlet pressures, at least one of the measured outlet pressures, and at least one of the measured confining pressures.

33 Claims, 5 Drawing Sheets

(56) References Cited

U.S. PATENT DOCUMENTS

| | | | |
|---|---|---|---|
| 4,749,038 | A | 6/1988 | Shelley et al. |
| 5,023,551 | A | 6/1991 | Kleinberg et al. |
| 5,193,396 | A | 3/1993 | Gorski |
| 5,387,865 | A | 2/1995 | Jerosch-Herold et al. |
| 5,435,187 | A | 7/1995 | Ewy |
| 5,486,762 | A | 1/1996 | Freedman et al. |
| 5,757,473 | A | 5/1998 | Kanduth et al. |
| 5,869,750 | A | 2/1999 | Onan |
| 6,012,520 | A | 1/2000 | Yu et al. |
| 7,091,719 | B2 | 8/2006 | Freedman |
| 7,703,531 | B2 | 4/2010 | Huang |
| 7,828,057 | B2 | 11/2010 | Kearl et al. |
| 8,584,755 | B2 | 11/2013 | Willberg |
| 8,646,524 | B2 | 2/2014 | Al-Buriak |
| 8,701,760 | B2 | 4/2014 | Parsche |
| 8,701,770 | B2 | 4/2014 | Schultz |
| 8,877,041 | B2 | 11/2014 | Parsche |
| 9,222,902 | B2 | 12/2015 | Gruber et al. |
| 9,653,812 | B2 | 5/2017 | Yan |
| 9,896,919 | B1 | 2/2018 | Chen |
| 10,047,281 | B2 | 8/2018 | Nguyen |
| 10,180,054 | B2 | 1/2019 | Chen |
| 10,202,827 | B2 | 2/2019 | Delchambre |
| 10,309,202 | B2 | 6/2019 | Soliman |
| 10,401,274 | B2 | 9/2019 | Liu et al. |
| 10,443,367 | B2 | 10/2019 | Chen |
| 10,571,384 | B2 | 2/2020 | Liu et al. |
| 10,837,278 | B2 | 11/2020 | Zhu et al. |
| 2001/0032055 | A1 | 10/2001 | Omar |
| 2003/0209248 | A1 | 11/2003 | Ward |
| 2005/0016732 | A1 | 1/2005 | Brannon |
| 2005/0059558 | A1 | 3/2005 | Blanch et al. |
| 2005/0103118 | A1 | 5/2005 | Workman |
| 2007/0054054 | A1 | 3/2007 | Svoboda et al. |
| 2008/0093073 | A1 | 4/2008 | Bustos et al. |
| 2008/0216559 | A1* | 9/2008 | Hilab .................... E21B 25/005 73/38 |
| 2009/0032252 | A1 | 2/2009 | Boney et al. |
| 2009/0095469 | A1 | 4/2009 | Dozier |
| 2009/0242196 | A1 | 10/2009 | Pao |
| 2009/0277634 | A1 | 11/2009 | Case |
| 2009/0283257 | A1 | 11/2009 | Becker |
| 2010/0154514 | A1 | 6/2010 | Algive |
| 2010/0243242 | A1 | 9/2010 | Boney et al. |
| 2010/0263867 | A1 | 10/2010 | Horton et al. |
| 2011/0083849 | A1 | 4/2011 | Medvedev |
| 2011/0108277 | A1 | 5/2011 | Dudley et al. |
| 2012/0018159 | A1 | 1/2012 | Gulta et al. |
| 2012/0061081 | A1 | 3/2012 | Sultenfuss et al. |
| 2012/0129737 | A1 | 5/2012 | Lesko et al. |
| 2012/0261129 | A1 | 10/2012 | Becker |
| 2012/0273193 | A1 | 11/2012 | Sen et al. |
| 2012/0318498 | A1 | 12/2012 | Parsche |
| 2013/0213120 | A1 | 8/2013 | Lebedev |
| 2013/0213638 | A1 | 8/2013 | Keller |
| 2013/0228019 | A1 | 9/2013 | Meadows |
| 2013/0233536 | A1 | 9/2013 | Alqam |
| 2013/0282386 | A1 | 10/2013 | Vilermo et al. |
| 2013/0290064 | A1 | 10/2013 | Altamirano et al. |
| 2014/0014327 | A1 | 1/2014 | Badri et al. |
| 2014/0027109 | A1 | 1/2014 | Al-Baraik |
| 2014/0221257 | A1 | 8/2014 | Roddy |
| 2014/0225607 | A1 | 8/2014 | Edwards |
| 2014/0239956 | A1 | 8/2014 | Hoversten |
| 2015/0055438 | A1 | 2/2015 | Okoniewski |
| 2015/0083420 | A1 | 3/2015 | Gupta et al. |
| 2015/0103624 | A1 | 4/2015 | Thompson |
| 2015/0112488 | A1 | 4/2015 | Hoehn et al. |
| 2015/0152724 | A1 | 6/2015 | Amendt |
| 2015/0167439 | A1 | 6/2015 | Kasevich et al. |
| 2015/0167440 | A1 | 6/2015 | Kasevich |
| 2015/0192005 | A1 | 7/2015 | Saeedfar |
| 2015/0300968 | A1 | 10/2015 | Bae et al. |
| 2015/0322759 | A1 | 11/2015 | Okoniewski |
| 2016/0103047 | A1 | 4/2016 | Liu |
| 2016/0103049 | A1 | 4/2016 | Liu |
| 2016/0170067 | A1 | 6/2016 | Heaton |
| 2016/0208602 | A1 | 7/2016 | Donderici et al. |
| 2016/0215205 | A1 | 7/2016 | Nguyen |
| 2016/0230549 | A1 | 8/2016 | Minh et al. |
| 2016/0341020 | A1 | 11/2016 | Al-Buriak |
| 2016/0379356 | A1 | 12/2016 | Louis |
| 2017/0016812 | A1 | 1/2017 | Liu et al. |
| 2017/0032078 | A1 | 2/2017 | Stelzer et al. |
| 2017/0145303 | A1 | 5/2017 | Fontenelle et al. |
| 2017/0167964 | A1 | 6/2017 | Liu et al. |
| 2017/0175505 | A1 | 6/2017 | Curlett |
| 2017/0370895 | A1 | 12/2017 | Han |
| 2018/0348111 | A1 | 12/2018 | Hannon |
| 2019/0226970 | A1 | 7/2019 | Dusterhoft et al. |
| 2020/0032636 | A1 | 1/2020 | Chen et al. |
| 2020/0363310 | A1* | 11/2020 | Zhang .................. G01N 33/241 |
| 2022/0042898 | A1 | 2/2022 | Zhao et al. |
| 2022/0056798 | A1 | 2/2022 | Zhang et al. |
| 2022/0214261 | A1* | 7/2022 | Liu ....................... E21B 49/008 |
| 2022/0214262 | A1* | 7/2022 | Liu ........................ G01N 33/24 |

FOREIGN PATENT DOCUMENTS

| | | |
|---|---|---|
| CN | 102183410 | 9/2011 |
| CN | 105784489 | 7/2016 |
| CN | 109975140 | 7/2019 |
| WO | WO 2012051647 | 4/2012 |
| WO | WO 2012057910 | 5/2012 |
| WO | WO 2013155061 | 10/2013 |
| WO | WO 2016163983 | 10/2016 |
| WO | WO-2021053193 A1 * | 3/2021 ......... G01N 15/0826 |

OTHER PUBLICATIONS

Alharbi, "Experimental Evaluation of the Effect of Carbonate Heterogeneity on Oil Recovery to Water and Gas Injections," University of Calgary, Sep. 9, 2013, 258 pages.

Alnoaimi and Kovscek, "Experimental and Numerical Analysis of Gas Transport in Shale including the Role of Sorption," SPE-166375, Society of Petroleum Engineers (SPE), presented at the SPE Annual Technical Conference and Exhibition, Sep. 30-Oct. 2, 2013, 16 pages.

Althaus et al., "Permeability Estimation of a Middle-East Tight Gas Sand with NMR Logs," URTec:2669857, Unconventional Resources Technology Conference (URTeC), proceedings of the 5th Unconventional Resources Technology Conference, Jul. 24, 2017, 7 pages.

Amabeoku et al., "Calibration of Permeability Derived from NMR Lobs in Carbonate Reservoirs," SPE 68085, Society of Petroleum Engineers (SPE), presented at the 2001 SPE Middle East Oil Show, Mar. 17-20, 2001, 11 pages.

An et al., "A new study of magnetic nanoparticle transport and quantifying magnetization analysis in fractured shale reservoir using numerical modeling," Journal of Natural Gas Science and Engineering, 28:502-521, Jan. 2016, 21 pages.

APMonitor.com [online], "Proportional integral derivative (PID)," Sep. 2020, retrieved Oct. 13, 2021 from URL<https://apmonitor.com/pdc/index.php/Main/ProportionalIntegralDerivative>, 3 pages.

Basu et al., "Best Practices for Shale Core Handling: Transportation, Sampling and Storage for Conduction of Analyses," Journal of Marine Science and Engineering, Feb. 2020, 8(2):136, 17 pages.

Bazant et al., "Size Effect in Brazilian Split-Cylinder Tests: Measurements and Fracture Analysis," ACI Materials Journal, 88:3 (325-332), May 31, 1991, 8 pages.

Bourbie and Walls, "Pulse decay permeability: analytical solution and experimental test," SPE Journal, 22:5, Oct. 1982, 11 pages.

Brace et al., "Permeability of granite under high pressure," Journal of Geophysics Res. 73:6, Mar. 15, 1968, 12 pages.

Brezovski and Cui, "Laboratory permeability measurements of unconventional reservoirs: useless or full of information? A montney example from the western canadian sedimentary basin," SPE-167047, Society of Petroleum Engineers (SPE), presented at the SPE Unconventional Resources Conference and Exhibition-Asia Pacific, Nov. 11-13, 2013, 12 pages.

(56) References Cited

OTHER PUBLICATIONS

Chen et al., "Assessing Tensile Strength of Unconventional Tight Rocks Using Microwaving," URTec: 2154488, Unconventional Resources Technology Conference (URTeC), presented at the Unconventional Resources Technology Conference, Jul. 20-22, 2015, San Antonio, Texas, USA, 12 pages.
Chen et al., "Fracturing Tight Rocks by Elevated Pore-Water Pressure Using Microwaving and its Applications," SPWLA 56th Annual Logging Symposium, Jul. 18-22, 2015, Long Beach, California, USA, 13 pages.
Chen et al., "Dependence of gas shale fracture permeability on effective stress and reservoir pressure: Model match and insights," Fuel, 2015, 139, 383-392, 10 pages.
Chen et al., "Optimization of NMR Permeability Transform and Application to Middle East Tight Sands," Society of Petrophysicists and Well-Log Analysts, SPWLA 58th Annual Logging Symposium, Jun. 17-21, 2017, 11 pages.
Civan et al., "Comparison of shale permeability to gas determined by pressure-pulse transmission testing of core plugs and crushed samples," Unconventional Resources Technology Conference, Jul. 2015, 1 page.
Clarkson et al., "Use of pressure- and rate-transient techniques for analyzing core permeability tests for unconventional reservoirs: Part 2," SPE Unconventional Resources Conference, Nov. 2013, 5 pages.
Cooper et al., "The effect of cracks on the thermal expansion of rocks," Earth and Planetary Science Letters, Oct. 1, 1977, 36(3):404-12, 9 pages.
Cronin, "Core-scale heterogeneity and dual-permeability pore structures in the Barnett Shale," Thesis for Degree of Master of Science in Geological Sciences at the University of Texas at Austin, Dec. 2014, 174 pages.
Cui et al., "Measurements of gas permeability and diffusivity of tight reservoir rocks: different approaches and their applications," Geofluids, 9:3, Aug. 2009, presented at the AAPG Convention, Jun. 7-10, 2009, 18 pages.
Darabi et al., "Gas flow in ultra-tight shale strata," Journal of Fluid Mechanics, 710, Nov. 10, 2012, 20 pages.
Dicker and Smits, "A practical approach for determining permeability from laboratory pressure-pulse decay measurements," SPE-17578, Society of Petroleum Engineers (SPE), presented at the SPE international Meeting on Petroleum Engineering, Nov. 1-4, 1988, 8 pages.
Egermann et al., "A fast and direct method of permeability measurements on drill cuttings," Society of Petroleum Engineers (SPE), SPE Reservoir Evaluation and Engineering, 8:4, Aug. 2005, 7 pages.
Finsterle and Persoff, "Determining permeability of tight rock samples using inverse modeling," Water Resources Research, 33:8, Aug. 1997, 9 pages.
Forni et al., "Conditioning Pre-existing Old Vertical Wells to Stimulate and Test Vaca Muerta Shale Productivity through the Application of Pinpoint Completion Techniques," SPE-172724-MS, Society of Petroleum Engineers (SPE), presented at the SPE middle East Oil and Gas Show and Conferences, Mar. 8-11, 2015, 28 pages.
George et al., "Approximate relationship between frequency-dependent skin depth resolved from geoelectromagnetic pedotransfer function and depth of investigation resolved from geoelectrical measurements: A case study of coastal formation, southern Nigeria," Journal of Earth System Science, Oct. 1, 2016, 125(7):1379-90, 12 pages.
Han and Cundall, "LBM-DEM modeling of fluid-solid interaction in porous media," International Journal for Numerical and Analytical Methods in Geomechanics, 37:10, Jul. 2013, 17 pages.
Heller et al., "Experimental investigation of matric permeability of gas shale," AAPG Bulletin, 98:5, May 2014, 21 pages.
Itascacg.com [online], "Particle Flow Code, Version 5.0," Itasca Consulting Group, Inc., available on or before Apr. 11, 2014, [retrieved on May 11, 2018], retrieved from URL: <https://www.itascacg.com/software/pfc>, 5 pages.

Jerath et al., "Improved assessment of in-situ fluid saturation with multi-dimensional NMR measurements and conventional well logs," SPWLA 53rd Annual Logging Symposium, Jun. 16-20, 2012, 16 pages.
Jianhong et al., "Estimation of the Tensile Elastic Modulus using Brazilian disc by Applying Diametrically Opposed Concentrated Loads," International Journal of Rock Mechanics & Mining Sciences, 46:3 (568-576), 2009, 9 pages.
Jones, "A Technique for Faster Pulse-Decay Permeability Measurements in Tight Rocks," presented at the 1994 SPE Annual Technical Conference and Exhibition, Sep. 25-28, 1994, SPE Formation Evaluation, Mar. 1997, 7 pages.
Kenyon, "Petrophysical Principles of Applications of NMR Logging," Society of Petrophyicists and Well-Log Analysts, 38:2, Mar. 1997, 23 pages.
Lai et al., "Experimental Investigation on Brazilian Tensile Strength of Organic-rich Gas Shale," SPE-177644-MS, Society of Petroleum Engineers (SPE), presented at the Abu Dhabi International Petroleum Exhibition and Conference, Nov. 9-12, 2015, 24 pages.
Li et al., "The Brazilian Disc Test for Rock Mechanics Applications: Review and New Insights," Rock Mech Rock Eng, 2013, 46: 269-287, 19 pages.
Liang et al., "An Experimental Study on interactions between Imbibed Fractured Fluid and Organic-Rich Tight Carbonate Source Rocks," SPE-188338-MS, Society of Petroleum Engineers (SPE), presented at the Abu Dhabi International Petroleum Exhibition and Conference, Nov. 13-16, 2017, 14 pages.
Liu, "Elastic constants determination and deformation observation using Brazilian disk geometry," presented at the XI International Congress and Exposition, Jun. 2-5, 2008, Experimental Mechanics, Sep. 1, 2010, 50(7):1025, 11 pages.
Luffel et al., "Matrix permeability measurement of gas productive shales," SPE-26633-MS, Society of Petroleum Engineers (SPE), presented at the 66th Annual Technical Conference and Exhibition, Oct. 3-6, 1993, 10 pages.
Metarocklab.com [online], "Pumps," 2019, retrieved Oct. 13, 2021 from URL<https://www.metarocklab.com/product-page/pressure-generators>, 2 pages.
Ning et al., "The measurement of Matrix and Fracture Properties in Naturally Fractured Cores," SPE-25898, Society of Petroleum Engineers (SPE), presented at the SPE Rocky Mountain Regional/Low Permeability Reservoirs Symposium, Apr. 26-28, 1993, 15 pages.
Paroscientific.com [online], "Overview & product selection guide," no date, retrieved Oct. 13, 2021 from URL<http://paroscientific.com/products.php>, 2 pages.
Pollard and Fletcher, "Fundamentals of Structural Geology," Cambridge University Press, Sep. 1, 2005, 291, 1 page.
ResTech, "Development of laboratory and petrophysical techniques for evaluating shale reservoirs," GRI-95/0496, Gas Research Institute, Apr. 1996, 306 pages.
Rydzy et al., "Stressed Permeability in Shales: Effects of Matrix Compressibility and Fractures—A Step Towards Measuring Matrix Permeability in Fractured Shale Samples," SCA2016-027, presented at the International Symposium of the Society of Core Analysts held in Snowmass, Colorado, USA, Aug. 21-26, 2016, 12 pages.
Shafer et al., "Protocols for Calibrating NMR Log-Derived Permeabilities," International Symposium of the Society of Core Analysts, Aug. 21, 2005, 15 pages.
Tang et al., "Impact of Stress-Dependent Matrix and Fracture Properties on Shale Gas Production," Energies, 10(7): 996, Jul. 2017, 13 pages.
Thomas et al., "Fractured reservoir simulation," SPE-9305-PA, Society of Petroleum Engineers (SPE), SPE Journal, 23:1, Feb. 1983, 13 pages.
Timur, "Effective Porosity and Permeability of Sandstones Investigated Through Nuclear Magnetic Resonance Principles," Society of Petrophysicists and Well-Log Analysts, presented at the SPWLA 9th Annual Logging Symposium, Jun. 23-26, 1968, 18 pages.
Trimmer et al., "Effect of pressure and stress on the water transport in intact and fractured gabbro and granite," Journal of Geophysical Research, 85, Dec. 10, 1980, 13 pages.

(56) References Cited

OTHER PUBLICATIONS

Wang et al., "The Flattened Brazilian Disc Specimen Used for Testing Elastic Modulus, Tensile Strength and Fracture Toughness of Brittle Rocks: Analytical and Numerical Results," Int J Rock Mech Min Sci 41(2): 245-253, 9 pages.

Warren and Root, "The behavior of naturally fractured reservoirs," SPE-426-PA, Society of Petroleum Engineers (SPE), SPE Journal, 3:3, Sep. 1963, 11 pages.

Waters, "Frac Fluids on Organic Shales: What We Know, What We Don't, and What Can We Do About It," Society of Petroleum Engineers (SPE) Asia Pacific Hydraulic Fracturing Conference, Aug. 24-26, 2016, Beijing, China, 29 pages.

Yaich et al.; "A Case Study: The Impact of Soaking on Well Performance in the Marcellus," SPE-178614-MS, URTeC: 2154766, Society of Petroleum Engineers (SPE), Unconventional Resources Technology Conference (URTeC), presented at the Unconventional Resources Technology Conference, Jul. 20-22, 2015, 11 pages.

Yamada and Jones, "A review of pulse technique for permeability measurements," SPE Journal, 20:5, Oct. 1980, 2 pages.

Yan et al., "General multi-porosity simulation for fractured reservoir modeling," Journal of Natural Gas Science Engineering, 33, Jul. 2016, 16 pages.

Zhang et al., "Matrix permeability measurement from fractured unconventional source-rock samples: Method and application," J Contam Hydrol, 233:103663, 2020, 6 pages.

Zheng et al., "Relationships between permeability, porosity and effective stress for low-permeability sedimentary rock," International Journal of Rock Mechanics and Mining Sciences, 78:304-318, 2015, 15 pages.

PCT International Search Report and Written Opinion in International Appln. No. PCT/US2021/046913, dated Dec. 7, 2021, 15 pages.

\* cited by examiner

| | Confining Pressure $p_c$ (psi) | Pore Pressure Range | Pressure in Upstream Reservoir $p_u$ (psi) | Pressure in Downstream Reservoir $p_d$ (psi) | $p_c - p_u$ | $p_c - p_d$ | Average of $p_c - p_u$ and $p_c - p_d$ |
|---|---|---|---|---|---|---|---|
| Run1 | 4500 | 2500-4000 | 4000 | 2500 | 500 | 2000 | 1200 |
| Run2 | 4500 | 2500-3330 | 3330 | 2500 | 1170 | 2000 | 1585 |
| Run3 | 5500 | 2500-4000 | 4000 | 2500 | 1500 | 3000 | 2250 |

500

| Run Name (302) | Confining Pressure $p_c$ (psi) (304) | Pore Pressure Range (306) | Pressure in Upstream Reservoir $p_u$ (psi) (308) | Pressure in Downstream Reservoir $p_d$ (psi) (310) | $p_c - p_u$ (312) | $p_c - p_d$ (314) | Average of $p_c - p_u$ and $p_c - p_d$ (316) |
|---|---|---|---|---|---|---|---|
| Run1 (301) | 4500 $p_{c1,1}$ | 2500-4000 | 4000 $p_{u1}$ | 2500 $p_{d1}$ | 500 | 2000 | 1200 |
| Run3 (305) | 5500 $p_{c1,1}$ | 2500-4000 | 4000 $p_{u1}$ | 2500 $p_{d1}$ | 1500 | 3000 | 2250 |

| Run Name (302) | Confining Pressure $p_c$ (psi) (304) | Pore Pressure Range (306) | Pressure in Upstream Reservoir $p_u$ (psi) (308) | Pressure in Downstream Reservoir $p_d$ (psi) (310) | $p_c - p_u$ (psi) (312) | $p_c - p_d$ (psi) (314) | Average of $p_c - p_u$ and $p_c - p_d$ (316) |
|---|---|---|---|---|---|---|---|
| Run1 (301) | 4500 $p_{c2}$ | 2500-4000 | 4000 $p_{u2,1}$ | 2500 $p_{d2}$ | 500 | 2000 | 1200 |
| Run2 (303) | 4500 $p_{c2}$ | 2500-3330 | 3330 $p_{u2,2}$ | 2500 $p_{d2}$ | 1170 | 2000 | 1585 |

FIG. 5B

DETERMINING ROCK PROPERTIES

TECHNICAL FIELD

The present disclosure describes apparatus, systems, and methods for determining rock properties.

BACKGROUND

Pore pressure of a subterranean reservoir, such as an unconventional reservoir, can decrease with hydrocarbon production. This can result in an increase in effective stress, or the difference between the overburden pressure and the pore pressure. In some cases, there is a linear relationship between the logarithm of the permeability and the effective stress that is important for predicting the hydrocarbon production.

SUMMARY

In an example implementation, a method for determining a rock property includes positioning a core sample in a core sample assembly that is enclosed in a pressurized container, the pressurized container includes a flow inlet, a flow outlet, and a pressurized fluid inlet fluidly coupled to a pressurized fluid reservoir that includes a pressurized fluid pump; sequentially performing at least three test operations on the core sample, each of the at least three test operations including flowing a test fluid into the flow inlet and flowing the test fluid out of the flow outlet, and flowing a pressurized fluid into the pressurized container from the pressurized fluid reservoir; at each of the at least three test operations, measuring an inlet pressure at the flow inlet, measuring an outlet pressure at the flow outlet, and measuring a confining pressure within the pressurized container; and determining a permeability of the core sample based at least in part on at least one of the measured inlet pressures, at least one of the measured outlet pressures, and at least one of the measured confining pressures.

In an aspect combinable with the example implementation, the at least three test operations includes a first test operation that includes operating a first pump to circulate the test fluid from a first reservoir, through the flow inlet, and to the core sample in the core sample assembly at a first inlet pressure, operating a second pump to circulate the test fluid from the core sample in the core sample assembly at a first outlet pressure, through the flow outlet, and to a second reservoir, and operating the pressurized fluid pump to circulate a pressurized fluid from the pressurized fluid reservoir to the pressurized container at a first confining pressure.

In another aspect combinable with any of the previous aspects, the at least three test operations includes a second test operation subsequent to the first test operation, the second test operation including operating the first pump to circulate the test fluid from the first reservoir, through the flow inlet, and to the core sample in the core sample assembly at a second inlet pressure different than the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at the first confining pressure.

In another aspect combinable with any of the previous aspects, the at least three test operations includes a third test operation subsequent to the first and second test operations, the third test operation including operating the first pump to circulate the test fluid from the first reservoir, through the flow inlet, and to the core sample in the core sample assembly at the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at a second confining pressure different than the first confining pressure.

In another aspect combinable with any of the previous aspects, determining a permeability of the core sample based at least in part on at least one of the measured inlet pressures, at least one of the measured outlet pressures, and at least one of the measured confining pressures includes determining a pressure dependence coefficient of the core sample based at least in part on the first inlet pressure, the first outlet pressure, and the first and second confining pressures.

In another aspect combinable with any of the previous aspects, determining the pressure dependence coefficient of the core sample based at least in part on the first inlet pressure, the first outlet pressure, and the first and second confining pressures includes determining the pressure dependence coefficient based on a first mass flow rate of the test fluid that is based on the first inlet pressure and the first outlet pressure, a second mass flow rate of the test fluid that is based on the first inlet pressure and the first outlet pressure, and a difference between the first and second confining pressures.

Another aspect combinable with any of the previous aspects further includes determining a poroelastic coefficient of the core sample based at least in part on the pressure dependence coefficient.

In another aspect combinable with any of the previous aspects, determining the poroelastic coefficient of the core sample based at least in part on the pressure dependence coefficient includes determining a product of the poroelastic coefficient and the pressure dependence coefficient based at least in part on a first mass flow rate of the test fluid that is based on the first inlet pressure and the first outlet pressure, a second mass flow rate of the test fluid that is based on the first inlet pressure and the first outlet pressure, the first and second inlet pressures, the first outlet pressure, and the first confining pressure; and determining the poroelastic coefficient from the product of the poroelastic coefficient and the pressure dependence coefficient.

Another aspect combinable with any of the previous aspects further includes determining the permeability of the core sample based at least in part on the poroelastic coefficient and the pressure dependence coefficient.

In another aspect combinable with any of the previous aspects, determining the permeability of the core sample based at least in part on the poroelastic coefficient and the pressure dependence coefficient includes determining the permeability of the core sample based at least in part on a first mass flow rate of the test fluid that is based on the first inlet pressure and the first outlet pressure; a cross-section area of the core sample; the poroelastic coefficient; the pressure dependence coefficient; a density of the test fluid; a viscosity of the test fluid; a distance between the flow inlet and the flow outlet; the first outlet pressure; and the first inlet pressure.

In another aspect combinable with any of the previous aspects, each of the measured inlet pressure, the measured outlet pressure, and the measured confining pressure is at a steady state condition.

In another example implementation, a system for determining a rock property includes a core sample assembly enclosed in a pressurized container that includes a flow inlet, a flow outlet, and a pressurized fluid inlet, the core sample assembly configured to secure a core sample; a pressurized fluid reservoir that includes a pressurized fluid pump, the pressurized fluid reservoir fluidly coupled to the pressurized fluid inlet; a first test fluid reservoir that includes a first pump, the first test fluid reservoir fluidly coupled to the flow inlet; a second test fluid reservoir that includes a second pump, the second test fluid reservoir fluidly coupled to the flow outlet; a plurality of fluid sensors, at least one fluid sensor positioned at or near each of the flow inlet, the flow outlet, and the pressurized fluid inlet; and a control system communicably coupled to the plurality of fluid sensors, the pressurized fluid pump, the first pump, and the second pump. The control system is configured to perform operations including operating the pressurized fluid pump, the first pump, and the second pump to sequentially perform at least three test operations on the core sample, each of the at least three test operations including flowing a test fluid into the flow inlet from the first test fluid reservoir and flowing the test fluid out of the flow outlet into the second test fluid reservoir, and flowing a pressurized fluid into the pressurized container from the pressurized fluid reservoir; at each of the at least three test operations, receiving, from the plurality of fluid sensors, measurements including an inlet pressure at the flow inlet, an outlet pressure at the flow outlet, and a confining pressure within the pressurized container; and determining a permeability of the core sample based at least in part on at least one of the measured inlet pressures, at least one of the measured outlet pressures, and at least one of the measured confining pressures.

In an aspect combinable with the example implementation, the at least three test operations include a first test operation that includes operating the first pump to circulate the test fluid from the first reservoir, through the flow inlet, and to the core sample in the core sample assembly at a first inlet pressure, operating the second pump to circulate the test fluid from the core sample in the core sample assembly at a first outlet pressure, through the flow outlet, and to the second reservoir, and operating the pressurized fluid pump to circulate the pressurized fluid from the pressurized fluid reservoir to the pressurized container at a first confining pressure.

In another aspect combinable with any of the previous aspects, the at least three test operations include a second test operation subsequent to the first test operation, the second test operation including operating the first pump to circulate the test fluid from the first reservoir, through the flow inlet, and to the core sample in the core sample assembly at a second inlet pressure different than the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at the first confining pressure.

In another aspect combinable with any of the previous aspects, the at least three test operations include a third test operation subsequent to the first and second test operations, the third test operation including operating the first pump to circulate the test fluid from the first reservoir, through the flow inlet, and to the core sample in the core sample assembly at the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at a second confining pressure different than the first confining pressure.

In another aspect combinable with any of the previous aspects, the operation of determining a permeability of the core sample based at least in part on at least one of the measured inlet pressures, at least one of the measured outlet pressures, and at least one of the measured confining pressures includes determining a pressure dependence coefficient of the core sample based at least in part on the first inlet pressure, the first outlet pressure, and the first and second confining pressures.

In another aspect combinable with any of the previous aspects, the operation of determining the pressure dependence coefficient of the core sample based at least in part on the first inlet pressure, the first outlet pressure, and the first and second confining pressures includes determining the pressure dependence coefficient based on a first mass flow rate of the test fluid that is based on the first inlet pressure and the first outlet pressure, a second mass flow rate of the test fluid that is based on the first inlet pressure and the first outlet pressure, and a difference between the first and second confining pressures.

In another aspect combinable with any of the previous aspects, the control system is configured to perform operations further including determining a poroelastic coefficient of the core sample based at least in part on the pressure dependence coefficient.

In another aspect combinable with any of the previous aspects, the operation of determining the poroelastic coefficient of the core sample based at least in part on the pressure dependence coefficient includes determining a product of the poroelastic coefficient and the pressure dependence coefficient based at least in part on a first mass flow rate of the test fluid that is based on the first inlet pressure and the first outlet pressure, a second mass flow rate of the test fluid that is based on the first inlet pressure and the first outlet pressure, the first and second inlet pressures, the first outlet pressure, and the first confining pressure; and determining the poroelastic coefficient from the product of the poroelastic coefficient and the pressure dependence coefficient.

In another aspect combinable with any of the previous aspects, the control system is configured to perform operations further including determining the permeability of the core sample based at least in part on the poroelastic coefficient and the pressure dependence coefficient.

In another aspect combinable with any of the previous aspects, the operation of determining the permeability of the core sample based at least in part on the poroelastic coefficient and the pressure dependence coefficient includes determining the permeability of the core sample based at least in part on a first mass flow rate of the test fluid that is based on the first inlet pressure and the first outlet pressure; a cross-section area of the core sample; the poroelastic coefficient; the pressure dependence coefficient; a density of the test fluid; a viscosity of the test fluid; a distance between the flow inlet and the flow outlet; the first outlet pressure; and the first inlet pressure.

In another aspect combinable with any of the previous aspects, each of the measured inlet pressure, the measured outlet pressure, and the measured confining pressure is at a steady state condition.

In another example implementation, an apparatus includes a tangible, non-transitory computer-readable media that includes instructions that, when executed by one or more hardware processors, cause the one or more hardware processors to perform operations including operating a core sample system to sequentially perform at least three test operations on a core sample, the core sample system including a core sample assembly that encloses the core sample and is enclosed in a pressurized container that includes a flow inlet, a flow outlet, and a pressurized fluid inlet; a pressurized fluid reservoir that includes a pressurized fluid pump fluidly coupled to the pressurized fluid inlet; a first test fluid reservoir that includes a first pump fluidly coupled to the flow inlet; a second test fluid reservoir that includes a second pump fluidly coupled to the flow outlet; and a plurality of fluid sensors, where each of the at least three test operations includes operating the first pump to flow a test fluid into the flow inlet from the first test fluid reservoir, operating the second pump to flow the test fluid out of the flow outlet into the second test fluid reservoir, and operating the pressurized fluid pump to flow a pressurized fluid into the pressurized container from the pressurized fluid reservoir; at each of the at least three test operations, identifying measurements from the plurality of fluid sensors positioned in the core sample system, the measurements including an inlet pressure at the flow inlet, an outlet pressure at the flow outlet, and a confining pressure within the pressurized container; and determining a permeability of the core sample based at least in part on at least one of the measured inlet pressures, at least one of the measured outlet pressures, and at least one of the measured confining pressures.

In an aspect combinable with the example implementation, the at least three test operations include a first test operation that includes operating the first pump to circulate the test fluid from the first reservoir, through the flow inlet, and to the core sample in the core sample assembly at a first inlet pressure, operating the second pump to circulate the test fluid from the core sample in the core sample assembly at a first outlet pressure, through the flow outlet, and to the second reservoir, and operating the pressurized fluid pump to circulate the pressurized fluid from the pressurized fluid reservoir to the pressurized container at a first confining pressure.

In another aspect combinable with any of the previous aspects, the at least three test operations include a second test operation subsequent to the first test operation, the second test operation including operating the first pump to circulate the test fluid from the first reservoir, through the flow inlet, and to the core sample in the core sample assembly at a second inlet pressure different than the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at the first confining pressure.

In another aspect combinable with any of the previous aspects, the at least three test operations include a third test operation subsequent to the first and second test operations, the third test operation including operating the first pump to circulate the test fluid from the first reservoir, through the flow inlet, and to the core sample in the core sample assembly at the first inlet pressure, operating the second pump to circulate the test fluid from the core sample in the core sample assembly at the first outlet pressure, through the flow outlet, and to the second reservoir, and operating the pressurized fluid pump to circulate the pressurized fluid from the pressurized fluid reservoir to the pressurized container at a second confining pressure different than the first confining pressure.

In another aspect combinable with any of the previous aspects, the operation of determining a permeability of the core sample based at least in part on at least one of the measured inlet pressures, at least one of the measured outlet pressures, and at least one of the measured confining pressures includes determining a pressure dependence coefficient of the core sample based at least in part on the first inlet pressure, the first outlet pressure, and the first and second confining pressures.

In another aspect combinable with any of the previous aspects, the operation of determining the pressure dependence coefficient of the core sample based at least in part on the first inlet pressure, the first outlet pressure, and the first and second confining pressures includes determining the pressure dependence coefficient based on a first mass flow rate of the test fluid that is based on the first inlet pressure and the first outlet pressure, a second mass flow rate of the test fluid that is based on the first inlet pressure and the first outlet pressure, and a difference between the first and second confining pressures.

In another aspect combinable with any of the previous aspects, the control system is configured to perform operations further including determining a poroelastic coefficient of the core sample based at least in part on the pressure dependence coefficient.

In another aspect combinable with any of the previous aspects, the operation of determining the poroelastic coefficient of the core sample based at least in part on the pressure dependence coefficient includes determining a product of the poroelastic coefficient and the pressure dependence coefficient based at least in part on a first mass flow rate of the test fluid that is based on the first inlet pressure and the first outlet pressure, a second mass flow rate of the test fluid that is based on the first inlet pressure and the first outlet pressure, the first and second inlet pressures, the first outlet pressure, and the first confining pressure; and determining the poroelastic coefficient from the product of the poroelastic coefficient and the pressure dependence coefficient.

In another aspect combinable with any of the previous aspects, the control system is configured to perform operations further including determining the permeability of the core sample based at least in part on the poroelastic coefficient and the pressure dependence coefficient.

In another aspect combinable with any of the previous aspects, the operation of determining the permeability of the core sample based at least in part on the poroelastic coefficient and the pressure dependence coefficient includes determining the permeability of the core sample based at least in part on a first mass flow rate of the test fluid that is based on the first inlet pressure and the first outlet pressure; a cross-section area of the core sample; the poroelastic coefficient; the pressure dependence coefficient; a density of the test fluid; a viscosity of the test fluid; a distance between the flow inlet and the flow outlet; the first outlet pressure; and the first inlet pressure.

In another aspect combinable with any of the previous aspects, each of the measured inlet pressure, the measured outlet pressure, and the measured confining pressure is at a steady state condition.

Implementations of a rock sample testing system according to the present disclosure may include one or more of the following features. For example, a rock sample testing system according to the present disclosure can save time and more efficiently determine one or more properties of a rock sample in a test system in a controlled environment. As another example, a rock sample testing system according to the present disclosure can operate without transducers mounted along a length of a rock sample in the test system, thereby eliminating sources of error. As another example, the analysis of the data from such a rock sample testing system according to the present disclosure provide a solution of several rock properties simultaneously, including but not limited to: the permeability, the dependence on effective stress, and a poroelastic constant.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIGS. 5A-5B are tables that describe measurements taken during an example experiment that tests a core sample according to the present disclosure.

DETAILED DESCRIPTION

Figure 1:
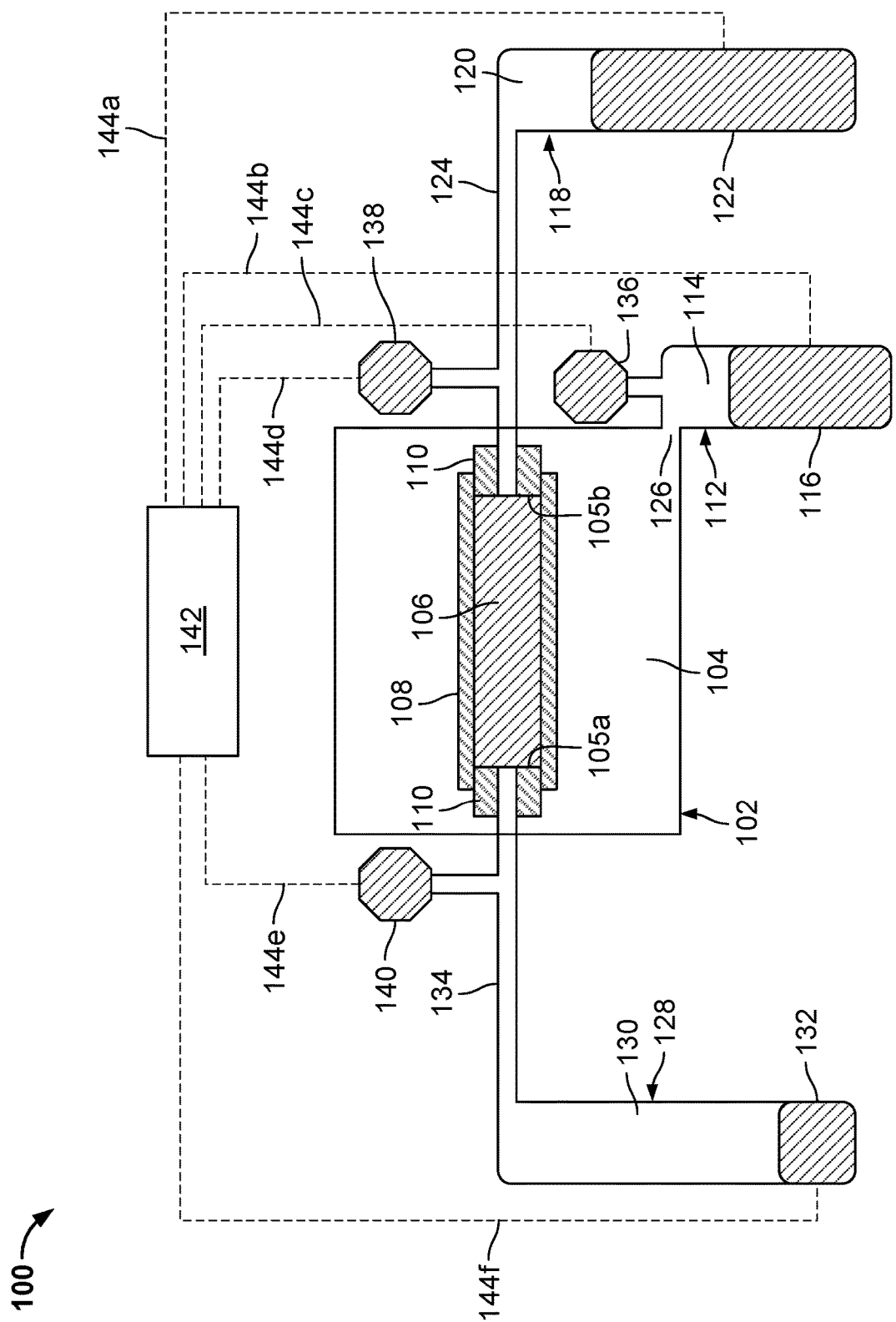
FIG. 1 is a schematic diagram of an example implementation of a core sample test system according to the present disclosure.

FIG. 1 is a schematic diagram of an example implementation of a core sample test system 100 according to the present disclosure. In some aspects, the core sample test system 100 can be operated to determine one or more characteristics or properties of a core sample 106 that is positioned within the system 100. Such characteristics include, for example, permeability, pressure dependent characteristics, as well as poroelastic characteristics. In some aspects, the core sample 106 comprises a shale rock sample taken from a subterranean formation; alternatively other types of rocks may also be used as the core sample 106, including rock samples from conventional and unconventional reservoirs.

As shown in FIG. 1, core sample test system 100 includes a core sample assembly 110 in which the core sample 106 is placed and secured. The core sample assembly 110 (or sample stack) includes a sleeve 108 that encircles the core sample 106, which in some aspects, is a cylindrical core sample with a diameter of 1 to 1.5 inches. In some aspects, prior to placing the core sample 106 within the core sample assembly 110, the core sample 106 is cut to between 1 and 2 inches long and pre-processed, e.g., to remove mobile water and hydrocarbon fluids therefrom. In some examples, the pre-processing includes trimming and polishing the end faces of the core sample 106 such that the two end faces are parallel to each other and perpendicular to the axis of the cylindrical core sample 106.

The core sample assembly 110 (including the core sample 106) is placed in a pressurized container 102 that defines a volume 104 in which the holder 110 is placed. As shown in this example, a pressurized fluid reservoir 112 (also called a confining reservoir) is fluidly coupled to the pressurized container 102 through a pressurized fluid inlet 126. Pressurized fluid reservoir 112 also includes or is in fluid communication with a pressurized fluid pump 116 that is operable to circulate a pressurized fluid 114 (e.g., a gas or other fluid) through the pressurized fluid inlet 126 and into the volume 104 to, e.g., controllably change or maintain a pressure of the volume 104 (sometimes called a confining pressure).

A flow inlet 134 is fluidly coupled to the core sample assembly 110 (and thus the core sample 106) through the pressurized container 102. The flow inlet 134 is also fluidly coupled to an upstream fluid reservoir 128. Upstream fluid reservoir 128 also includes or is in fluid communication with an upstream fluid pump 132 that is operable to circulate a test fluid 130 (e.g., a gas or other fluid) through the flow inlet 134 and into the core sample assembly 110 to, e.g., controllably change or maintain a pressure at a first end (e.g., an upstream end) of the core sample 106.

A flow outlet 124 is fluidly coupled to the core sample assembly 110 (and thus the core sample 106) through the pressurized container 102. The flow outlet 124 is also fluidly coupled to a downstream fluid reservoir 118. Downstream fluid reservoir 118 also includes or is in fluid communication with a downstream fluid pump 122 that is operable to circulate a test fluid 120 (which can be the same fluid as test fluid 130) through the flow outlet 134 from the core sample assembly 110 to, e.g., controllably change or maintain a pressure at a second end (e.g., a downstream end) of the core sample 106. In the present disclosure, one or more of the described fluid pumps can be, for example, a high accuracy pressure gas pump, such as MetaRock's 30 cc gas pumps with a volume resolution of $2.46 \times 10^{-6}$ cc (https://www.metarocklab.com/product-page/pressure-generators).

The core sample test system 100 includes fluid sensors 136, 138, and 140, as well as fluid pumps 116, 122, and 132. Each of the fluid sensors 136-140 can be operable to measure a characteristics, such as pressure, temperature, or a combination thereof, of a fluid flow within the core sample test system 100. Each of the fluid pumps among 116, 122, and 132 can be operable to measure a characteristics, such as the volume, volume change, the volume change with time (e.g., flow rate), or a combination thereof, of a fluid flow within the core sample test system 100. For example, fluid sensor 136 is positioned and operable to measure a characteristic (e.g., pressure) of pressurized fluid 114, which in turn can be identical to or substantially the same as a confining pressure of volume 104. Fluid sensor 138 is positioned and operable to measure a characteristic (e.g., pressure) of test fluid 120, which in turn can be identical to or substantially the same as a flow outlet pressure of the flow outlet 124. Fluid sensor 140 is positioned and operable to measure a characteristic (e.g., pressure) of test fluid 130, which in turn can be identical to or substantially the same as a flow inlet pressure of the flow inlet 134. Each of the fluid sensors 136-140 can be, for example, a high accuracy, high precision sensor, such as Paroscientific Inc.'s 9000-10k-101 transducers that are capable of measuring both pressure and temperature simultaneously (http://paroscientific.com/products.php).

As shown in FIG. 1, a control system (or controller) 142 is communicably coupled to components of the system 100. Control system 142, in some aspects, can be a PID controller (https://apmonitor.com/pdc/index.php/Main/ProportionalIntegralDerivative). For example, as shown, the control system 142 is communicably coupled to the fluid pumps 116, 122, and 132 to control operation (e.g., speed, on/off) of each fluid pump individually. Control of fluid pumps 116, 122, and 132 can be through control lines 144a, 144b, and 144f, respectively. Control system 142 is also communicably coupled to the fluid sensors 136, 138, and 140 through control lines 144c, 144d, and 144e, respectively, to receive measurements (e.g., pressure, temperature, flow rate, or a combination thereof). In some aspects, control system 142 is a microprocessor-based system that includes one or more hardware processors, one or more memory modules that store executable instructions (e.g., in MatLab code), and one or more communication or network interfaces to allow communication between the control system 142 and the fluid pumps and fluid sensors shown in FIG. 1. Although not shown, additional components, such as valves (e.g., modulating or shut-off), power supplies, and/or pump motors can also be included within the system 100 for operation.

Notably, operation of the core sample test system 100 in this example implementation of FIG. 1 avoids a "point by point measurement" approach, in which one test run of the system 100 would only provide one permeability data point and all test runs are lengthy processes by themselves. In addition, for each measurement in a point-by-point measurement approach requires a lengthy period of preparation process. The use of the point-by-point measurement (in other words, a conventional approach) is often due to the requirement of data analysis that inside a core sample there must be a small pressure difference such that gas properties, such as the compressibility, density, and viscosity, can be approximated as constants.

In addition, operation of the core sample test system 100 in this example implementation of FIG. 1 avoids single or multiple transducers installed on the flow path of the core sample (i.e., between the two ends of a core sample). For instance, as shown, the core sample assembly 110 is exclusive of any pressure or temperature transducer. The connection between the transducers and the core sample can require high dexterity to mount and can be a potential weak point to cause leaks between the confining fluid and the pore (or test) fluid.

In addition, as described in more detail herein, operation of the core sample test system 100 utilizes a steady state method, e.g., the pressure at a particular location in the core sample test system 100 does not appreciably change with time once in steady state. Also, by using, e.g., a relatively large pressure difference across core sample 106 (e.g., 1500 psi) as compared to that of conventional steady state systems (e.g., 10 s of psi) allows for the steady state operation of core sample test system 100 and associated methods.

Figure 2:
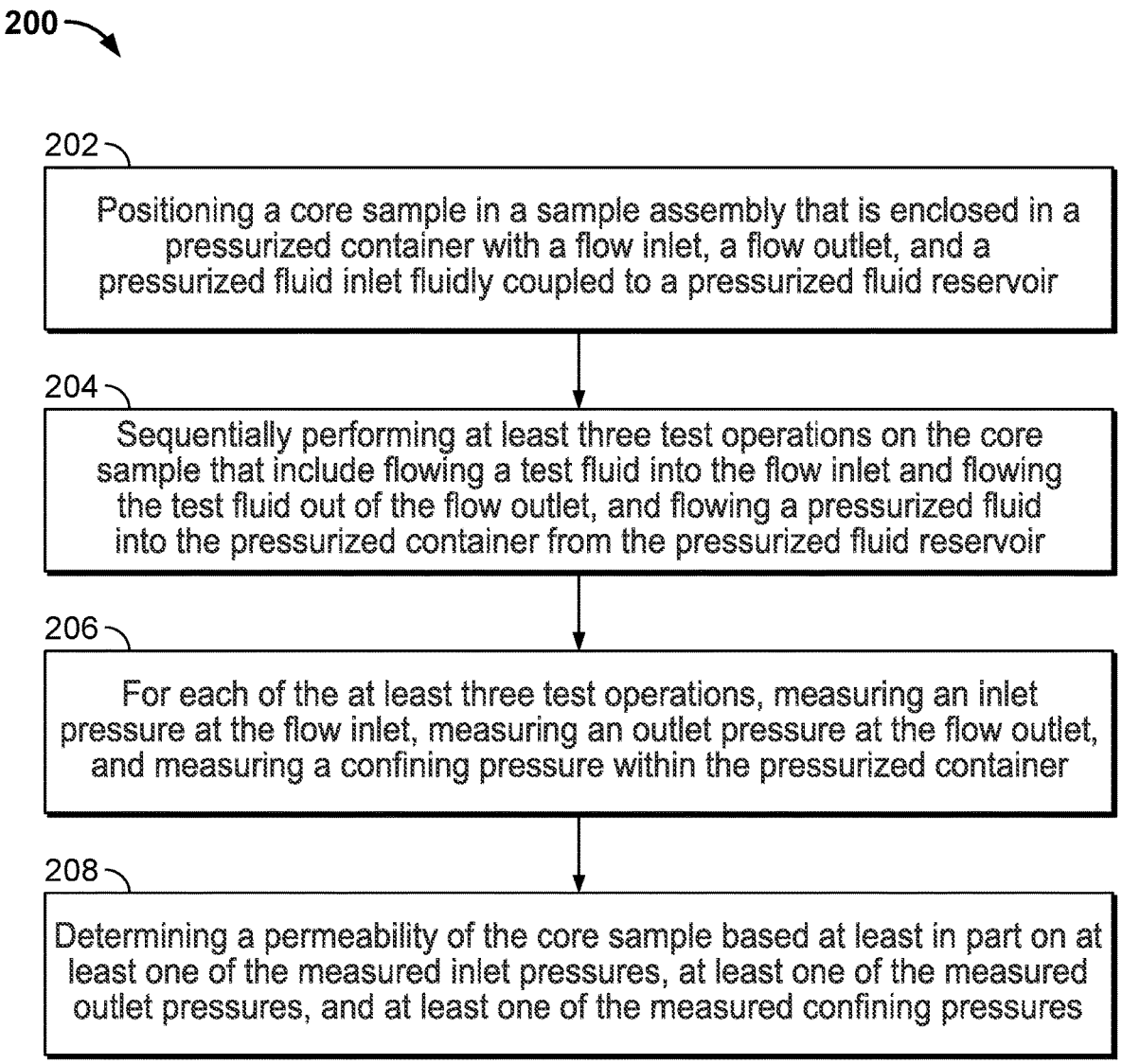
FIG. 2 is a flowchart of an example method performed with or by the example implementation of the core sample test system of FIG. 1.

FIG. 2 is a flowchart of an example method performed with or by the example implementation of the core sample test system 100 of FIG. 1. Generally, method 200 can be implemented and comprise at least three operational runs of steady state experiments with different pressure differences between the upstream fluid reservoir 128 and downstream fluid reservoir 118 and/or different confining pressures in the volume 104. In such steady-state measurement tests, the upstream and downstream pressures (in flow inlet 134 and flow outlet 124, respectively) can be kept constant (or substantially constant) at selected pressures with the control system 142.

Method 200 can begin at step 202, which includes positioning a core sample in a core sample assembly (or sample stack) that is enclosed in a pressurized container with a flow inlet, a flow outlet, and a pressurized fluid inlet fluidly coupled to a pressurized fluid reservoir. For example, as shown in FIG. 1, the core sample 106 is placed in the core sample assembly 110 and enclosed by sleeve 108 around a radial surface of (in this example) the cylindrically-shaped sample 106. In this example, therefore, axial faces 105a and 105b of the core sample 106 are exposed to the flow inlet 134 and the flow outlet 124, respectively. The core sample assembly 110, as shown, is positioned in the volume 104 of the pressurized container 102 and thus exposed to the pressure of the pressurized gas 114 at the pressurized fluid inlet 126. In some aspects, it is ensured that there is no detected leakage from all the connections to the sample 106 within the pressurized container 102 such that there is no fluid exchange between the pressurized gas 114 and the fluid flowing through the sample from 130 to 120.

Method 200 can continue at step 204, which includes sequentially performing at least three test operations on the core sample that include flowing a test fluid into the flow inlet and flowing the test fluid out of the flow outlet, and flowing a pressurized fluid into the pressurized container from the pressurized fluid reservoir. For example, each test operation comprises operation of the upstream fluid pump 132, the downstream fluid pump 122, and the pressurized fluid pump 116 to provide or maintain a particular upstream pressure at the axial face 105a, a particular downstream pressure at the axial face 105b, and a particular confining pressure in the volume 104.

The three test operations can be viewed to comprise two pairs of operations: a first pair of test operations can include a first test run and a third test run, while a second pair of test operations can include the first test run and a second test run. In other example implementations, the pairing of test runs can be changed e.g., a first pair of test operations can include the first test run and the second test run, while a second pair of test operations can include the first test run and the third test run).

In this example implementation of method 200, the test runs in the first pair can have the same (or substantially similar) upstream pressures (at the axial face 105a) and the same (or substantially similar) downstream pressures (at the axial face 105b) but different confining pressures in the volume 104. The second pair of the test runs can have the same confining pressures in volume 104 and the same fluid pressures in one reservoir (i.e., at one axial face of the core sample 106), such as the upstream flow reservoir 128 or downstream flow reservoir 118, but different fluid pressures in the other reservoir (i.e., at the other axial face of the core sample 106).

In some aspects of method 200, to avoid effects of hysteresis, a sequence of the three test runs can be conducted so that an effective stress of the core sample 106 can keep increasing or decreasing during the three test runs.

Method 200 can continue at step 206, which includes, for each of the at least three test operations, measuring an inlet pressure at the flow inlet, measuring an outlet pressure at the flow outlet, and measuring a confining pressure within the pressurized container; and perform these measurement until the experiment reaches the steady state. For example, as shown in Table 300 in FIG. 3, measurements can be taken by the fluid sensors 136, 138, and 140 to measure a characteristic (such as pressure, temperature, or flow rate or a combination thereof) of a particular fluid in the core sample test system 100. For example, flow sensor 140 measures, in this example, a pressure in the flow inlet 134 (and thus at the axial face 105a). Flow sensor 138 measures, in this example, a pressure in the flow outlet 124 (and thus at the axial face 105b). Flow sensor 136 measures, in this example, a pressure in the pressurized fluid inlet 126 (and thus in volume 104).

Table 300 shows, in columns 302-316 left to right: Test Run Number (302); confining pressure (304) (pressure in volume 104), $p_c$; "pore" pressure range (306) (i.e., a range between upstream pressure at axial face 105a and downstream pressure at axial face 105b); a pressure (308) in upstream flow reservoir 128, $p_u$; a pressure (310) in downstream flow reservoir 118, pa; a difference in confining pressure and upstream pressure (312); a difference in confining pressure and downstream pressure (314); and an average of the differences (316) shown in the previous two columns. The measured and determined pressure values of the first, second, and third test runs are shown in rows 301, 303, and 305, respectively.

In this example of method 200, therefore, a first pair of test runs, test run 1 and test run 3, share an upstream pressure, $p_u$, of 4,000 psi and a downstream pressure, $p_d$, of 2,500 psi, but have different confining pressures ($p_c$) of 4500 psi and 5500 psi, respectively. A second pair of test runs, test run 1 and test run 2, share the same downstream pressure, $p_d$, of 2,500 psi; the same confining pressure, $p_c$, of 4500 psi, but different upstream pressure, $p_u$, 3330 psi and 4000 psi, respectively. In this example, the test run order (test run 1, then test run 2, then test run 3) is chosen to ensure that the effective stress keeps increasing from one test to the next, as suggested by the average of the pressure differences (316) in Table 300. Further, for a steady-state flow test run (such as test runs 1, 2, and 3), the gas pressure at the inlet of the core sample 106 (i.e., within the flow inlet 134 at axial face 105a) is the same as the pressure in the upstream fluid reservoir 128, $p_u$, and is kept constant or substantially constant. The gas pressure at the outlet of the core sample 106 (i.e., within the flow outlet 124 at axial face 105b) is the same as the pressure in the downstream fluid reservoir 118, $p_d$, and is kept constant or substantially constant. In some aspects of method 200, it is assumed that the tubing connected to the inlet and outlet of a core sample is assumed to produce no resistance to the flow (or its permeability is assumed to be infinitely large).

For each test, pre-specified or desired constant gas pressures are achieved and maintained in the upstream and downstream fluid reservoirs 128 and 118, respectively, as well as the pressurized fluid reservoir 112. Then, the test fluid 130 flows from the flow inlet 134 to the flow outlet 124, because the inlet gas pressure, $p_u$, is higher than the outlet gas pressure, $p_d$. The steady state stipulates that no pressure at any point within the sample 106 changes with time. After the steady state flow process is achieved along the rock sample, a mass flow rate, Q, of the test fluid 130 (and therefore test fluid 120) is independent of time. In some aspects, when an apparent average permeability (as determined in step 208) does not change more than 5% within a particular time duration (e.g., four hours or another selected time duration), the steady state flow condition is achieved.

Method 200 can continue at step 208, which includes determining a permeability of the core sample based at least in part on at least one of the measured inlet pressures, at least one of the measured outlet pressures, and at least one of the measured confining pressures. For example, in some aspects, determination of the apparent permeability of the core sample 106 is based at least in part on an average of the upstream and downstream flow rates in mass and Darcy's law, which can be used to calculate a permeability (e.g., an apparent average permeability) of the core sample 106.

In some aspects, other characteristics of the core sample 106 can be determined prior to determination of the apparent average permeability, such as a pressure dependence coefficient, $\alpha$, and a poroelastic coefficient, $\beta$, of the core sample 106. In some aspects, determining these other characteristics starts with Darcy's law:

$$Q = -A\frac{k\rho}{\mu}\frac{\delta p}{\delta x} \qquad (1)$$

where Q is the mass flow rate, A is the area of a cross-section of the core sample 106 (in m²), k is permeability (in m²), $\rho$ and $\mu$ are gas density (in kg/m³) and viscosity (Pa-sec), respectively, p is gas pressure in Pascal, and x is a spatial coordinate (in m) along the core sample with zero value at the axial face 105a.

Integrating Eq. 1 from the axial face 105a (x=0) to the axial face 105b (x=L, length of the core sample 106) yields:

$$\int_0^L Qdx = -A\int_{p_u}^{p_d} \frac{k\rho}{\mu}dp. \qquad (2)$$

Since Q is a constant at steady state (of the test runs 1, 2, and 3), Eq. 2 becomes:

$$\frac{QL}{A} = \int_{p_d}^{p_u} \frac{k\rho}{\mu}dp. \qquad (3)$$

In some aspects, the permeability is an exponential function of effective stress. Thus, $k_0$ can be used for the permeability when the effective stress equals to 0, and $k_d$ and $k_u$ can be the permeabilities of the core sample 106 when the pore pressures are $p_d$ and $p_u$, respectively. Then relationships between permeability and pressure are given as follows:

$k_d = k_0 \exp[-\alpha(p_c - \beta p_d)]$ for $x=L$ (4), $k_x = k_0 \exp[-\alpha(p_c - \beta p_x)]$ for $0 < x < L$ (5), and $k_u = k_0 \exp[-\alpha(p_c - \beta p_u)]$ for $x=0$ (6).

Based on the three relationships of Eqs. 4-6:

$k_x = k_d \exp[-\alpha \oplus (p_d - p_x)] = k_d \exp[\alpha\beta(p_x - p_d)]$ (7), and $k_x = k_u \exp[-\alpha\beta(p_u - p_x)]$ (8).

The flow of the test fluid 130 (and test fluid 120) can be described by the constant parameters of $\alpha$ and $\beta$, as well as one of $k_d$ or $k_u$. These three parameters can be determined by the test runs of step 204. Inserting Eq. 7 into Eq. 3 yields:

$$\frac{QL}{A} = k_d \int_{p_d}^{p_u} \frac{\exp[-\alpha\beta(p_d - p)]\rho dp}{\mu}. \qquad (9)$$

Similar equations can be written for $k_u$ and $p_u$ by combining Eq. 8 and Eq. 3.

In some aspects, the pressure measurements from test runs 1 and 3 (i.e., the first test pair) can be used to determine the pressure dependence coefficient, $\alpha$. Then, once $\alpha$ is known, the poroelastic coefficient, $\beta$, can be determined.

Once both α and β are determined, the permeability of the core sample 106, e.g., the permeability at axial face 105b, $k_d$, can be calculated.

For example, turning to FIGS. 5A-5B, these figures show tables 500 and 505, each of which shows a portion of the table 300. Table 500 shows the portion of the table 300 that corresponds to the first pair of test runs (test run 1 and test run 3). Table 505 shows the portion of the table 300 that corresponds to the second pair of test runs (test run 1 and test run 2). The sub-script nomenclature used in tables 500 and 505 is as follows: the comma-separated paired number subscripts refer to the number of the test run pair and the test run number, while a single number subscript indicates the number of the test run pair. Thus, in table 500, column 304, row 301, $p_{c1,1}$ refers to the measured confining pressure, $p_c$, in the volume 104 during the first pair of test runs and during the first test run of that pair.

As mentioned, the first pair of test runs (test run 1 and test run 3, i.e., tests 301 and 305 in tables 300 and 500, respectively) can be used to determine the pressure dependence coefficient, a. As shown in table 500, the first pair of two test runs have different confining pressures $p_{c1,1}$ and $p_{c1,2}$ respectively, and the same $p_{d1}$ and $p_{u1}$ for each test run in the pair. From Eq. 9, therefore:

$$\frac{Q_{1,1}L}{A} = k_{d1,1} \int_{p_{d1}}^{p_{u1}} \frac{\exp[\alpha\beta(p - p_{d1})]\rho dp}{\mu} \text{ when } p_c = p_{c1,1}, \quad (10)$$

and $$\frac{Q_{1,2}L}{A} = k_{d1,2} \int_{p_{d1}}^{p_{u1}} \frac{\exp[\alpha\beta(p - p_{d1})]\rho dp}{\mu} \text{ when } p_c = p_{c1,2}. \quad (11)$$

From Eqs. 10 and 11:

$$\frac{Q_{1,1}}{Q_{1,2}} = \frac{k_{d1,1}}{k_{d1,2}}. \quad (12)$$

Then from Eq. 4, $k_{d1,1} = k_0 \exp[-\alpha(p_{c1,1} - \beta p_{d1})]$, and $k_{d1,2} = k_0 \exp[-\alpha(p_{c1,2} - \beta p_{d1})]$ collectively (13).

From Eq. 13, $$\frac{k_{d1,1}}{k_{d1,2}} = \exp(-\alpha(p_{c1,1} - p_{c1,2})). \quad (14)$$

Where $k_0$ is the permeability of the core sample when the effective stress is zero, and the two subscripts are the test pair number and test run number, e.g., $Q_{1,2}$ is for the mass flow rate for pair 1 run 2. by combining Eqs. 12-14, the stress sensitivity factor, a, sometimes expressed in the unit of 1/pascal or 1/psi, for describing the permeability's dependence on effective stress:

$$\alpha = \frac{\ln \frac{Q_{1,1}}{Q_{1,2}}}{p_{c1,2} - p_{c1,1}}. \quad (15)$$

Once α is determined, then the product, αβ, can be determined using the second pair of the two test runs (test run 1 and test run 2, i.e., tests 301 and 303 in tables 300 and 505, respectively) that have the same confining pressure, $p_{c2}$, the same downstream pressure, $p_{d2}$, but different upstream pressures ($p_{u2,1}$ and $p_{u2,2}$). This example implementation changes the upstream pressure between test run 1 and test run 2; alternatively, the downstream pressures of test runs 1 and 2 can be different while the upstream pressure remains the same in test runs 1 and 2 and the same solution can be found.

Again, from Eq. 4:

$$\frac{Q_{2,1}L}{A} = k_{d2} \int_{p_{d2}}^{p_{u2,1}} \frac{\exp[\alpha\beta(p - p_{d2})]\rho dp}{\mu}, \quad (16)$$

and $$\frac{Q_{2,2}L}{A} = k_{d2} \int_{p_{d2}}^{p_{u2,2}} \frac{\exp[\alpha\beta(p - p_{d2})]\rho dp}{\mu}. \quad (17)$$

Dividing Eq. 16 by Eq. 17 gives:

$$\frac{Q_{2,1}}{Q_{2,2}} = \frac{\int_{p_{d2}}^{p_{u2,1}} \frac{\exp[\alpha\beta(p - p_{d2})]\rho dp}{\mu}}{\int_{p_{d2}}^{p_{u2,2}} \frac{\exp[\alpha\beta(p - p_{d2})]\rho dp}{\mu}}. \quad (18)$$

In Eq. 18, the only unknown parameter is the product, αβ. The pressure (p) and mass flow rates (Q) are all measured or determined by measurements with the control system 142. The test fluid density and viscosity are also known for the test fluid used in the test runs. Thus, the product, αβ, can be determined by solving for this in Eq. 18. As a is calculated from Eq. 15, then the poroelastic coefficient, β, can be determined. After estimating the stress sensitivity parameter, the permeability of the core sample 106 (e.g., the permeability at the axial face 105b, $k_{d2}$ or the permeability at any other conditions $k_{d1}$, $k_{u1}$, $k_{u2,1}$, $k_{u2,2}$, or $k_0$) can be calculated by Eq. 16, 13, 4, or 6, or the combination thereof.

Method 200 can include additional steps as well. For example, once the permeability (e.g., stress-dependent permeability) is determined for the core sample 106, a hydrocarbon production rate from a reservoir from which the sample 106 came can be predicted. For example, during the hydrocarbon production from an unconventional reservoir, the pore pressure decreases with time and thus effective stress will change with time as well. In that case, permeability will be a function of both time and location as a result of stress alteration during the production. The stress-dependent permeability determined in step 208 can be used as an input into a reservoir simulator to more accurately predict the hydrocarbon production because the measured stress dependency captures the permeability evolution during the production. The determined and predicted parameters of the core sample 106 can be graphically represented on a GUI of the control system 142.

Figures 3, 4:
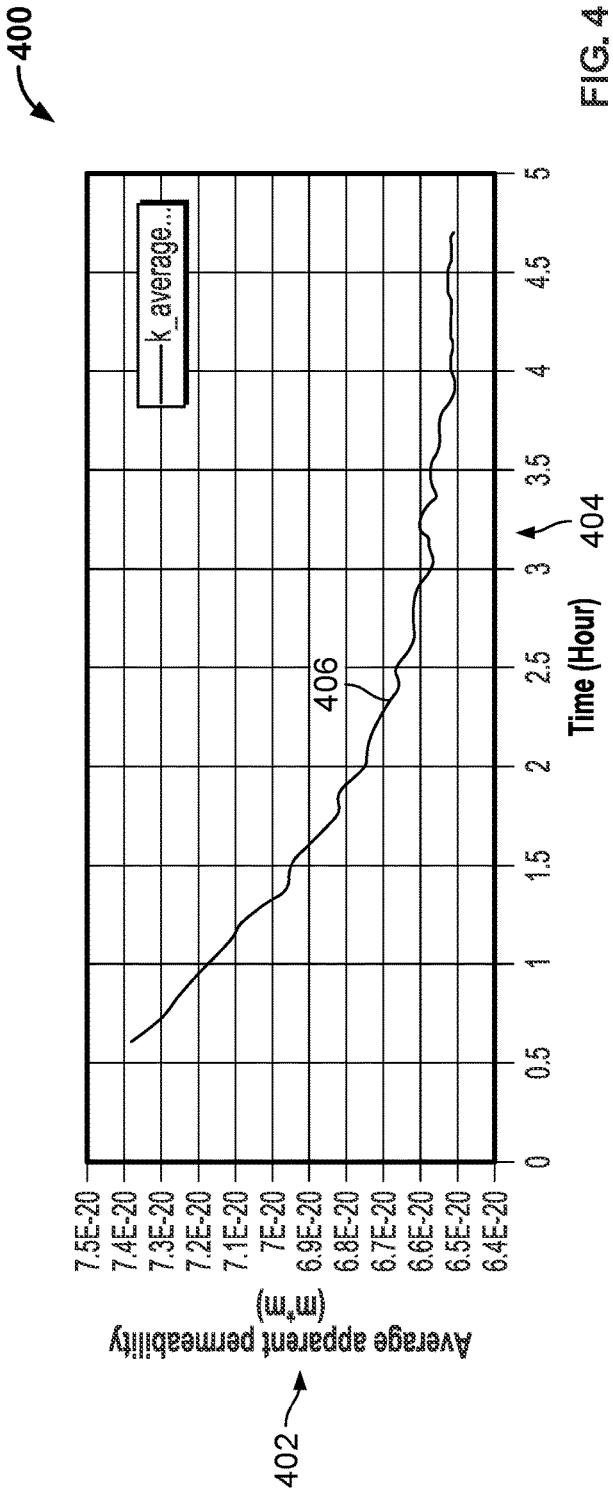
FIG. 3 is a table that describes measurements taken during an example method for testing a core sample according to the present disclosure.
FIG. 4 is a graph that describes a core sample property determined during an example method for testing a core sample according to the present disclosure.

The tables 500 and 505 show actual experimental test runs and results using a core sample test system 100 according to the present disclosure. The test runs 1, 2, and 3 described in tables 500 and 505 were used to demonstrate a determination of the parameters of the core sample 106 of α, β, $k_{d1}$, and $k_{d2}$. The test runs were conducted such that the apparent permeability (using steady state method, assuming one permeability through the core sample) changed within a tolerance level. FIG. 4 is a graph 400 that describes a calculated apparent permeability, k_average, during a time period of the test runs 1, 2, and 3 described in tables 500 and 505 (as well as table 300).

Graph 400 includes a y axis that describes average apparent permeability in m². X-axis 404 shows test run time in hours. The curve 406 represent the calculated apparent permeability, k_average. In this example, each test run (1, 2, and 3) lasted about 4-10 hours. Graph 400 shows that the apparent average permeability after three hours is 6.6E-20 m² and at four hours is 6.5E-20 m². The curve 406 shows about a 41.5% change. Using the measurements shown in table 500, as well as determined flow rate measurements of $Q_{1,1}$ of 2.0177e-7 kg/s for test run 1 and $Q_{1,2}$ of 1.2601E-7 kg/s for test run 3, the pressure dependence coefficient, a, was calculated by Eq. 15 of 4.7078E-4 psi⁻. Next, using table 505 and the second pair of test runs (test run 1 and test run 2), flow rates $Q_{2,1}$ of 2.0177E-7 kg/s and $Q_{2,2}$ of 5.5691E-8 kg/s were calculated. Then, with the value of α being determined already, the poroelastic coefficient, β, is determined to be 0.83 with Eq. 18.

The permeability of the core sample 106 at a particular condition can then be determined. Using the calculated α and β, as well as the measured pressures of test run 1, Eq. 10 yields a flow rate $Q_{1,1}$ of 2.0177E-7 kg/s. Then using Eq. 18, $k_{d1,1}$ is determined to be 8.616E-20 m². Thus, the permeability of the core sample 106 is at 8.616E-20 m² when the pore pressure (pressure at the axial face 105b or in the downstream fluid reservoir 118) is at 2500 psi, while the nominal effective stress is 2000 psi (confining pressure in the volume 104 of 4500 psi minus the pore pressure 2500 psi).

Figure 6:
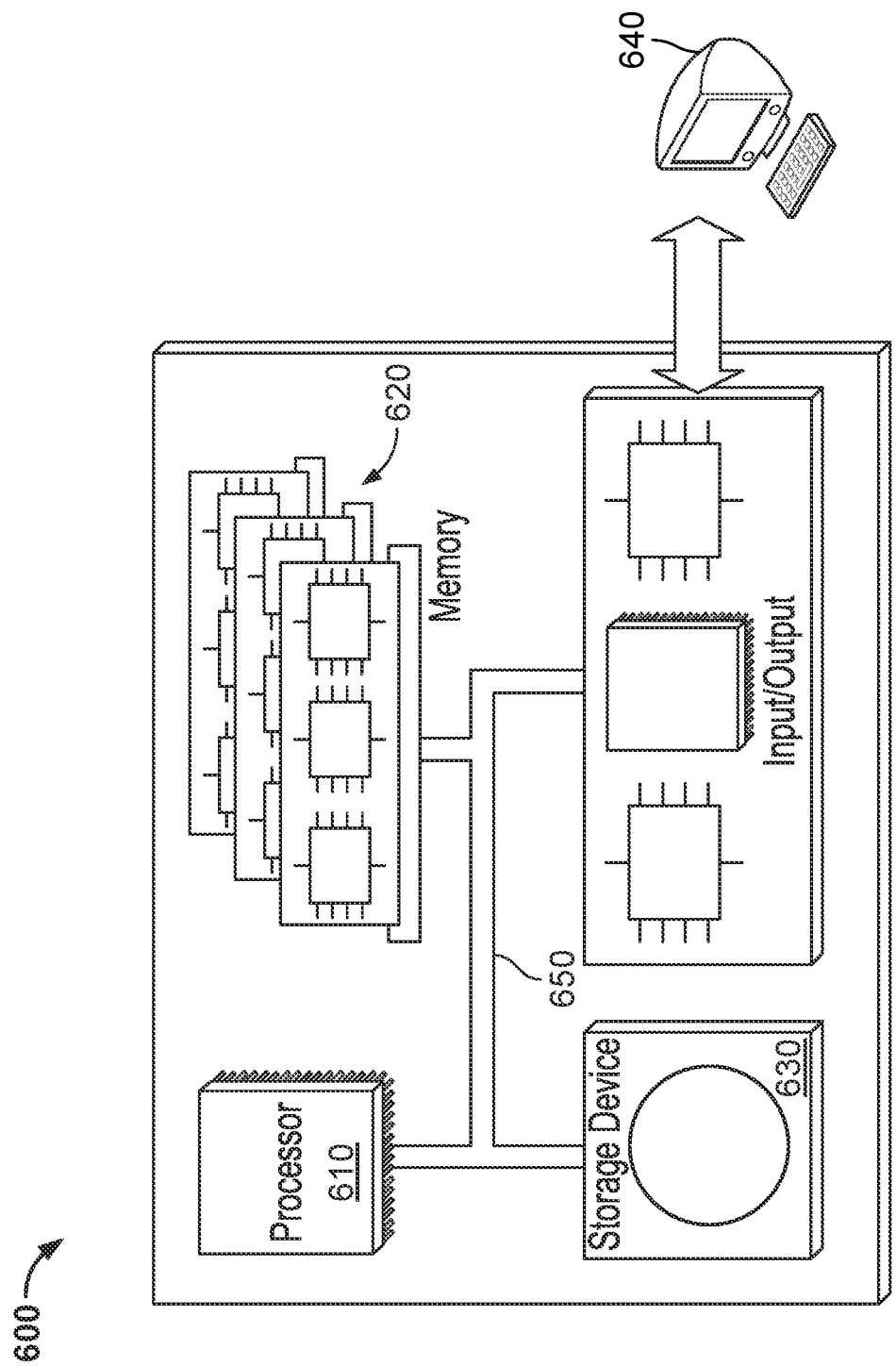
FIG. 6 is a schematic illustration of an example controller (or control system) for a core sample test system according to the present disclosure.

FIG. 6 is a schematic illustration of an example controller 600 (or control system) for operating a core sample test system, such as all or a portion of core sample test system 100 of FIG. 1. For example, all or parts of the controller 600 can be used for the operations described previously, for example as or as part of the control system 142. The controller 600 is intended to include various forms of digital computers, such as printed circuit boards (PCB), processors, digital circuitry, or otherwise. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 600 includes a processor 610, a memory 620, a storage device 630, and an input/output device 640. Each of the components 610, 620, 630, and 640 are interconnected using a system bus 650. The processor 610 is capable of processing instructions for execution within the controller 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the controller 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the controller 600. In one implementation, the storage device 630 is a computer-readable medium. In various different implementations, the storage device 630 may be a floppy disk device, a hard disk device, an optical disk device, a tape device, flash memory, a solid state device (SSD), or a combination thereof.

The input/output device 640 provides input/output operations for the controller 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for determining a rock property, comprising:
    positioning a core sample in a core sample assembly that is enclosed in a pressurized container, the pressurized container comprises a flow inlet, a flow outlet, and a pressurized fluid inlet fluidly coupled to a pressurized fluid reservoir that comprises a pressurized fluid pump;
    sequentially performing at least three test operations on the core sample, each of the at least three test operations comprising flowing a test fluid into the flow inlet and flowing the test fluid out of the flow outlet, and flowing a pressurized fluid into the pressurized container from the pressurized fluid reservoir;
    at each of the at least three test operations, measuring an inlet pressure at the flow inlet, measuring an outlet pressure at the flow outlet, and measuring a confining pressure within the pressurized container; and
    determining a permeability of the core sample based at least in part on at least one of the measured inlet pressures, at least one of the measured outlet pressures, and at least one of the measured confining pressures.

2. The method of claim 1, wherein the at least three test operations comprises a first test operation that comprises:
    operating a first pump to circulate the test fluid from a first reservoir, through the flow inlet, and to the core sample in the core sample assembly at a first inlet pressure,
    operating a second pump to circulate the test fluid from the core sample in the core sample assembly at a first outlet pressure, through the flow outlet, and to a second reservoir, and
    operating the pressurized fluid pump to circulate a pressurized fluid from the pressurized fluid reservoir to the pressurized container at a first confining pressure.

3. The method of claim 2, wherein the at least three test operations comprises a second test operation subsequent to the first test operation, the second test operation comprising:
    operating the first pump to circulate the test fluid from the first reservoir, through the flow inlet, and to the core sample in the core sample assembly at a second inlet pressure different than the first inlet pressure,
    operating the second pump to circulate the test fluid from the core sample in the core sample assembly at the first outlet pressure, through the flow outlet, and to the second reservoir, and
    operating the pressurized fluid pump to circulate the pressurized fluid from the pressurized fluid reservoir to the pressurized container at the first confining pressure.

4. The method of claim 3, wherein the at least three test operations comprises a third test operation subsequent to the first and second test operations, the third test operation comprising:
    operating the first pump to circulate the test fluid from the first reservoir, through the flow inlet, and to the core sample in the core sample assembly at the first inlet pressure,
    operating the second pump to circulate the test fluid from the core sample in the core sample assembly at the first outlet pressure, through the flow outlet, and to the second reservoir, and
    operating the pressurized fluid pump to circulate the pressurized fluid from the pressurized fluid reservoir to the pressurized container at a second confining pressure different than the first confining pressure.

5. The method of claim 4, wherein determining a permeability of the core sample based at least in part on at least one of the measured inlet pressures, at least one of the measured outlet pressures, and at least one of the measured confining pressures comprises:
    determining a pressure dependence coefficient of the core sample based at least in part on the first inlet pressure, the first outlet pressure, and the first and second confining pressures.

6. The method of claim 5, wherein determining the pressure dependence coefficient of the core sample based at least in part on the first inlet pressure, the first outlet pressure, and the first and second confining pressures comprises:

determining the pressure dependence coefficient based on:
  a first mass flow rate of the test fluid that is based on the first inlet pressure and the first outlet pressure,
  a second mass flow rate of the test fluid that is based on the first inlet pressure and the first outlet pressure, and
  a difference between the first and second confining pressures.

7. The method of claim 5, further comprising determining a poroelastic coefficient of the core sample based at least in part on the pressure dependence coefficient.

8. The method of claim 7, wherein determining the poroelastic coefficient of the core sample based at least in part on the pressure dependence coefficient comprises:
  determining a product of the poroelastic coefficient and the pressure dependence coefficient based at least in part on:
    a first mass flow rate of the test fluid that is based on the first inlet pressure and the first outlet pressure,
    a second mass flow rate of the test fluid that is based on the first inlet pressure and the first outlet pressure,
    the first and second inlet pressures,
    the first outlet pressure, and
    the first confining pressure; and
  determining the poroelastic coefficient from the product of the poroelastic coefficient and the pressure dependence coefficient.

9. The method of claim 7, further comprising determining the permeability of the core sample based at least in part on the poroelastic coefficient and the pressure dependence coefficient.

10. The method of claim 9, wherein determining the permeability of the core sample based at least in part on the poroelastic coefficient and the pressure dependence coefficient comprises determining the permeability of the core sample based at least in part on:
  a first mass flow rate of the test fluid that is based on the first inlet pressure and the first outlet pressure;
  a cross-section area of the core sample;
  the poroelastic coefficient;
  the pressure dependence coefficient;
  a density of the test fluid;
  a viscosity of the test fluid;
  a distance between the flow inlet and the flow outlet;
  the first outlet pressure; and
  the first inlet pressure.

11. The method of claim 1, wherein each of the measured inlet pressure, the measured outlet pressure, and the measured confining pressure is at a steady state condition.

12. A system for determining a rock property, comprising:
  a core sample assembly enclosed in a pressurized container that includes a flow inlet, a flow outlet, and a pressurized fluid inlet, the core sample assembly configured to secure a core sample;
  a pressurized fluid reservoir that comprises a pressurized fluid pump, the pressurized fluid reservoir fluidly coupled to the pressurized fluid inlet;
  a first test fluid reservoir that comprises a first pump, the first test fluid reservoir fluidly coupled to the flow inlet;
  a second test fluid reservoir that comprises a second pump, the second test fluid reservoir fluidly coupled to the flow outlet;
  a plurality of fluid sensors, at least one fluid sensor positioned at or near each of the flow inlet, the flow outlet, and the pressurized fluid inlet; and
  a control system communicably coupled to the plurality of fluid sensors, the pressurized fluid pump, the first pump, and the second pump, the control system configured to perform operations comprising:
    operating the pressurized fluid pump, the first pump, and the second pump to sequentially perform at least three test operations on the core sample, each of the at least three test operations comprising flowing a test fluid into the flow inlet from the first test fluid reservoir and flowing the test fluid out of the flow outlet into the second test fluid reservoir, and flowing a pressurized fluid into the pressurized container from the pressurized fluid reservoir;
    at each of the at least three test operations, receiving, from the plurality of fluid sensors, measurements comprising an inlet pressure at the flow inlet, an outlet pressure at the flow outlet, and a confining pressure within the pressurized container; and
    determining a permeability of the core sample based at least in part on at least one of the measured inlet pressures, at least one of the measured outlet pressures, and at least one of the measured confining pressures.

13. The system of claim 12, wherein the at least three test operations comprise a first test operation that comprises:
  operating the first pump to circulate the test fluid from the first reservoir, through the flow inlet, and to the core sample in the core sample assembly at a first inlet pressure,
  operating the second pump to circulate the test fluid from the core sample in the core sample assembly at a first outlet pressure, through the flow outlet, and to the second reservoir, and
  operating the pressurized fluid pump to circulate the pressurized fluid from the pressurized fluid reservoir to the pressurized container at a first confining pressure.

14. The system of claim 13, wherein the at least three test operations comprise a second test operation subsequent to the first test operation, the second test operation comprising:
  operating the first pump to circulate the test fluid from the first reservoir, through the flow inlet, and to the core sample in the core sample assembly at a second inlet pressure different than the first inlet pressure,
  operating the second pump to circulate the test fluid from the core sample in the core sample assembly at the first outlet pressure, through the flow outlet, and to the second reservoir, and
  operating the pressurized fluid pump to circulate the pressurized fluid from the pressurized fluid reservoir to the pressurized container at the first confining pressure.

15. The system of claim 14, wherein the at least three test operations comprise a third test operation subsequent to the first and second test operations, the third test operation comprising:
  operating the first pump to circulate the test fluid from the first reservoir, through the flow inlet, and to the core sample in the core sample assembly at the first inlet pressure,
  operating the second pump to circulate the test fluid from the core sample in the core sample assembly at the first outlet pressure, through the flow outlet, and to the second reservoir, and
  operating the pressurized fluid pump to circulate the pressurized fluid from the pressurized fluid reservoir to the pressurized container at a second confining pressure different than the first confining pressure.

16. The system of claim 15, wherein the operation of determining a permeability of the core sample based at least in part on at least one of the measured inlet pressures, at least one of the measured outlet pressures, and at least one of the measured confining pressures comprises:
determining a pressure dependence coefficient of the core sample based at least in part on the first inlet pressure, the first outlet pressure, and the first and second confining pressures.

17. The system of claim 16, wherein the operation of determining the pressure dependence coefficient of the core sample based at least in part on the first inlet pressure, the first outlet pressure, and the first and second confining pressures comprises:
determining the pressure dependence coefficient based on:
a first mass flow rate of the test fluid that is based on the first inlet pressure and the first outlet pressure,
a second mass flow rate of the test fluid that is based on the first inlet pressure and the first outlet pressure, and
a difference between the first and second confining pressures.

18. The system of claim 16, wherein the control system is configured to perform operations further comprising determining a poroelastic coefficient of the core sample based at least in part on the pressure dependence coefficient.

19. The system of claim 18, wherein the operation of determining the poroelastic coefficient of the core sample based at least in part on the pressure dependence coefficient comprises:
determining a product of the poroelastic coefficient and the pressure dependence coefficient based at least in part on:
a first mass flow rate of the test fluid that is based on the first inlet pressure and the first outlet pressure,
a second mass flow rate of the test fluid that is based on the first inlet pressure and the first outlet pressure,
the first and second inlet pressures,
the first outlet pressure, and
the first confining pressure; and
determining the poroelastic coefficient from the product of the poroelastic coefficient and the pressure dependence coefficient.

20. The system of claim 18, wherein the control system is configured to perform operations further comprising determining the permeability of the core sample based at least in part on the poroelastic coefficient and the pressure dependence coefficient.

21. The system of claim 20, wherein the operation of determining the permeability of the core sample based at least in part on the poroelastic coefficient and the pressure dependence coefficient comprises determining the permeability of the core sample based at least in part on:
a first mass flow rate of the test fluid that is based on the first inlet pressure and the first outlet pressure;
a cross-section area of the core sample;
the poroelastic coefficient;
the pressure dependence coefficient;
a density of the test fluid;
a viscosity of the test fluid;
a distance between the flow inlet and the flow outlet;
the first outlet pressure; and
the first inlet pressure.

22. The system of claim 12, wherein each of the measured inlet pressure, the measured outlet pressure, and the measured confining pressure is at a steady state condition.

23. An apparatus comprising a tangible, non-transitory computer-readable media that comprises instructions that, when executed by one or more hardware processors, cause the one or more hardware processors to perform operations comprising:
operating a core sample system to sequentially perform at least three test operations on a core sample, the core sample system comprising a core sample assembly that encloses the core sample and is enclosed in a pressurized container that includes a flow inlet, a flow outlet, and a pressurized fluid inlet; a pressurized fluid reservoir that comprises a pressurized fluid pump fluidly coupled to the pressurized fluid inlet; a first test fluid reservoir that comprises a first pump fluidly coupled to the flow inlet; a second test fluid reservoir that comprises a second pump fluidly coupled to the flow outlet; and a plurality of fluid sensors, where each of the at least three test operations comprises:
operating the first pump to flow a test fluid into the flow inlet from the first test fluid reservoir,
operating the second pump to flow the test fluid out of the flow outlet into the second test fluid reservoir, and
operating the pressurized fluid pump to flow a pressurized fluid into the pressurized container from the pressurized fluid reservoir;
at each of the at least three test operations, identifying measurements from the plurality of fluid sensors positioned in the core sample system, the measurements comprising an inlet pressure at the flow inlet, an outlet pressure at the flow outlet, and a confining pressure within the pressurized container; and
determining a permeability of the core sample based at least in part on at least one of the measured inlet pressures, at least one of the measured outlet pressures, and at least one of the measured confining pressures.

24. The apparatus of claim 23, wherein the at least three test operations comprise a first test operation that comprises:
operating the first pump to circulate the test fluid from the first reservoir, through the flow inlet, and to the core sample in the core sample assembly at a first inlet pressure,
operating the second pump to circulate the test fluid from the core sample in the core sample assembly at a first outlet pressure, through the flow outlet, and to the second reservoir, and
operating the pressurized fluid pump to circulate the pressurized fluid from the pressurized fluid reservoir to the pressurized container at a first confining pressure.

25. The apparatus of claim 24, wherein the at least three test operations comprise a second test operation subsequent to the first test operation, the second test operation comprising:
operating the first pump to circulate the test fluid from the first reservoir, through the flow inlet, and to the core sample in the core sample assembly at a second inlet pressure different than the first inlet pressure,
operating the second pump to circulate the test fluid from the core sample in the core sample assembly at the first outlet pressure, through the flow outlet, and to the second reservoir, and
operating the pressurized fluid pump to circulate the pressurized fluid from the pressurized fluid reservoir to the pressurized container at the first confining pressure.

26. The apparatus of claim 25, wherein the at least three test operations comprise a third test operation subsequent to the first and second test operations, the third test operation comprising:
- operating the first pump to circulate the test fluid from the first reservoir, through the flow inlet, and to the core sample in the core sample assembly at the first inlet pressure,
- operating the second pump to circulate the test fluid from the core sample in the core sample assembly at the first outlet pressure, through the flow outlet, and to the second reservoir, and
- operating the pressurized fluid pump to circulate the pressurized fluid from the pressurized fluid reservoir to the pressurized container at a second confining pressure different than the first confining pressure.

27. The apparatus of claim 26, wherein the operation of determining a permeability of the core sample based at least in part on at least one of the measured inlet pressures, at least one of the measured outlet pressures, and at least one of the measured confining pressures comprises:
- determining a pressure dependence coefficient of the core sample based at least in part on the first inlet pressure, the first outlet pressure, and the first and second confining pressures.

28. The apparatus of claim 27, wherein the operation of determining the pressure dependence coefficient of the core sample based at least in part on the first inlet pressure, the first outlet pressure, and the first and second confining pressures comprises:
- determining the pressure dependence coefficient based on:
  - a first mass flow rate of the test fluid that is based on the first inlet pressure and the first outlet pressure,
  - a second mass flow rate of the test fluid that is based on the first inlet pressure and the first outlet pressure, and
  - a difference between the first and second confining pressures.

29. The apparatus of claim 27, wherein the control system is configured to perform operations further comprising determining a poroelastic coefficient of the core sample based at least in part on the pressure dependence coefficient.

30. The apparatus of claim 29, wherein the operation of determining the poroelastic coefficient of the core sample based at least in part on the pressure dependence coefficient comprises:
- determining a product of the poroelastic coefficient and the pressure dependence coefficient based at least in part on:
  - a first mass flow rate of the test fluid that is based on the first inlet pressure and the first outlet pressure,
  - a second mass flow rate of the test fluid that is based on the first inlet pressure and the first outlet pressure,
  - the first and second inlet pressures,
  - the first outlet pressure, and
  - the first confining pressure; and
- determining the poroelastic coefficient from the product of the poroelastic coefficient and the pressure dependence coefficient.

31. The apparatus of claim 29, wherein the control system is configured to perform operations further comprising determining the permeability of the core sample based at least in part on the poroelastic coefficient and the pressure dependence coefficient.

32. The apparatus of claim 31, wherein the operation of determining the permeability of the core sample based at least in part on the poroelastic coefficient and the pressure dependence coefficient comprises determining the permeability of the core sample based at least in part on:
- a first mass flow rate of the test fluid that is based on the first inlet pressure and the first outlet pressure;
- a cross-section area of the core sample;
- the poroelastic coefficient;
- the pressure dependence coefficient;
- a density of the test fluid;
- a viscosity of the test fluid;
- a distance between the flow inlet and the flow outlet;
- the first outlet pressure; and
- the first inlet pressure.

33. The apparatus of claim 23, wherein each of the measured inlet pressure, the measured outlet pressure, and the measured confining pressure is at a steady state condition.

* * * * *